(12) United States Patent
Cheng et al.

(10) Patent No.: US 9,733,210 B2
(45) Date of Patent: Aug. 15, 2017

(54) NANOFLUID SENSOR WITH REAL-TIME SPATIAL SENSING

(71) Applicant: International Business Machines Corporation, Armonk, NY (US)

(72) Inventors: Kangguo Cheng, Schenectady, NY (US); Ali Khakifirooz, Los Altos, CA (US); Ghavam G. Shahidi, Pound Ridge, NY (US); Davood Shahrjerdi, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 130 days.

(21) Appl. No.: 14/587,941

(22) Filed: Dec. 31, 2014

(65) Prior Publication Data
US 2016/0187288 A1  Jun. 30, 2016

(51) Int. Cl.
*H01L 21/84* (2006.01)
*H01L 27/12* (2006.01)
*G01N 27/414* (2006.01)

(52) U.S. Cl.
CPC ......... *G01N 27/4145* (2013.01); *H01L 21/84* (2013.01); *H01L 27/1203* (2013.01); *G01N 27/4146* (2013.01); *G01N 27/4148* (2013.01)

(58) Field of Classification Search
CPC .......... G01N 27/4145; G01N 27/4146; G01N 27/4148
See application file for complete search history.

(56) References Cited

U.S. PATENT DOCUMENTS

| | | | |
|---|---|---|---|
| 5,343,064 A | * | 8/1994 | Spangler ............ B81C 1/00246 257/350 |
| 7,781,167 B2 | | 8/2010 | Lim et al. |
| 7,824,530 B2 | | 11/2010 | Yoo et al. |
| 7,825,037 B2 | | 11/2010 | Brueck et al. |
| 7,863,140 B2 | | 1/2011 | Lim et al. |
| 8,080,152 B2 | | 12/2011 | Sirringhaus |
| 8,303,789 B1 | | 11/2012 | Ivory et al. |

(Continued)

FOREIGN PATENT DOCUMENTS

| | | |
|---|---|---|
| EP | 1715932 | 11/2006 |
| EP | 2216396 A1 | 8/2010 |

(Continued)

*Primary Examiner* — Kevin Parendo
(74) *Attorney, Agent, or Firm* — Scully, Scott, Murphy & Presser, P.C.; Louis J. Percello, Esq.

(57) ABSTRACT

A semiconductor structure capable of real-time spatial sensing of nanoparticles within a nanofluid is provided. The structure includes an array of gate structures. An interlevel dielectric material surrounds the array of gate structures. A vertical inlet channel is located within a portion of the interlevel dielectric material and on one side of the array of gate structures. A vertical outlet channel is located within another portion of the interlevel dielectric material and on another side of the array of gate structures. A horizontal channel that functions as a back gate is in fluid communication with the vertical inlet and outlet channels, and is located beneath the array of gate structures. A back gate dielectric material portion lines exposed surfaces within the vertical inlet channel, the vertical outlet channel and the horizontal channel.

14 Claims, 7 Drawing Sheets

(56) References Cited

U.S. PATENT DOCUMENTS

| | | | |
|---|---|---|---|
| 8,728,844 B1* | 5/2014 | Liu | H01L 29/66477 257/252 |
| 2005/0089924 A1 | 4/2005 | Ho et al. | |
| 2005/0212016 A1 | 9/2005 | Brunner et al. | |
| 2007/0031961 A1 | 2/2007 | Ho et al. | |
| 2010/0248284 A1* | 9/2010 | Chen | G01N 33/48728 435/29 |
| 2010/0327847 A1* | 12/2010 | Leiber | B82Y 15/00 324/71.1 |
| 2011/0192724 A1 | 8/2011 | Han et al. | |
| 2011/0227043 A1* | 9/2011 | Guo | H01L 29/42384 257/24 |
| 2011/0227558 A1 | 9/2011 | Mannion et al. | |
| 2012/0024700 A1* | 2/2012 | Boccardi | G01N 27/4145 204/403.01 |
| 2012/0268804 A1 | 10/2012 | Hadwen | |
| 2012/0288672 A1 | 11/2012 | Ogilvie et al. | |
| 2013/0026030 A1 | 1/2013 | Ivory et al. | |
| 2014/0203332 A1 | 7/2014 | Cheng et al. | |
| 2014/0239986 A1* | 8/2014 | Liu | G01R 1/07307 324/750.01 |
| 2015/0083597 A1* | 3/2015 | Mohammadi | G01N 33/48721 204/603 |
| 2015/0129937 A1* | 5/2015 | Chen | G01N 27/4145 257/253 |
| 2016/0178568 A1* | 6/2016 | Cheng | G01N 27/4148 257/253 |

FOREIGN PATENT DOCUMENTS

| | | |
|---|---|---|
| EP | 1575867 B1 | 5/2011 |
| EP | 2470297 | 7/2012 |
| EP | 2475612 | 7/2012 |
| EP | 2078045 B1 | 9/2012 |
| EP | 2514529 A2 | 10/2012 |
| EP | 2524381 | 11/2012 |
| JP | 2012202864 | 10/2012 |
| WO | WO2005079944 | 9/2005 |
| WO | WO2008050109 A1 | 5/2008 |
| WO | WO2011023949 A2 | 3/2011 |
| WO | WO2011031959 A1 | 3/2011 |
| WO | WO2011087913 A1 | 7/2011 |
| WO | WO2012091540 A1 | 7/2012 |

* cited by examiner

NANOFLUID SENSOR WITH REAL-TIME SPATIAL SENSING

BACKGROUND

The present application relates to a semiconductor structure and a method of forming the same. More particularly, the present application relates to a semiconductor structure containing an array of gate structures, i.e., field effect transistors, located above a nanofluid channel which can be used for real-time spatial sensing of nano-sized particles within a nanofluid.

A biomolecule is any molecule that is produced by a living organism, including large macromolecules such as proteins, polysaccharides, lipids, and nucleic acids, as well as small molecules such as primary metabolites, secondary metabolites, and natural products. Detection of biomolecules such as, for example, proteins and viruses play an important role in healthcare and drug discovery.

Traditionally, biomolecules are detected using florescene or isotope labeling and patch clamp. These traditional biomolecule detection methods have limited sensitivity and automation. Also, the traditional biomolecule detection methods exhibit slow response time and require large amounts of reagent, which may not always be available.

Recently, field effect transistor (FET) sensors have been proposed for biosensing. Most FET based sensors are planar and provide improved biosensing capabilities over their traditionally used biomolecule detection methods. In a typical planar FET based sensor, the sensor is used for sensing charged molecules or ions, which cause a change in the drain current of the planar FET sensor when the charged species are brought into proximity with the channel region of the FET sensor.

Despite providing improved biosensing capability over the traditional biomolecule detection methods mentioned above, there is a need for further improvements within FET based sensors. In particular, there is a need for providing FET based sensors which are capable of real-time spatial sensing of nanoparticles such as bimolecular nanoparticles that are contained within a nanofluid.

SUMMARY

A semiconductor structure capable of real-time spatial sensing of nanoparticles within a nanofluid is provided. The structure includes an array of gate structures (i.e., field effect transistors, FETs). A vertical inlet channel is located within a portion of the interlevel dielectric material and on one side of the array of gate structures. A vertical outlet channel is located within another portion of the interlevel dielectric material and on another side of the array of gate structures. A horizontal channel that functions as a back gate is in fluid communication with the vertical inlet and outlet channels, and is located beneath the array of gate structures. A back gate dielectric material portion lines exposed surfaces within the vertical inlet channel, the vertical outlet channel and the horizontal channel.

In one aspect of the present application, a semiconductor structure that is capable of real-time spatial sensing of nanoparticles within a nanofluid is provided. In one embodiment of the present application, the semiconductor structure includes an array of gate structures, wherein each gate structure of the array of gate structures is located on a semiconductor material portion. An interlevel dielectric material surrounds the array of gate structures. A vertical inlet channel is located within a portion of the interlevel dielectric material and located on one side of the array of gate structures. A vertical outlet channel is located within another portion of the interlevel dielectric material and located on another side of the array of gate structures. A horizontal channel is connected to the vertical inlet and outlet channels, and is located beneath the array of gate structures. The horizontal channel also vertically separates the array of gate structures from an underlying handle substrate. A back gate dielectric material portion lines exposed surfaces within the vertical inlet channel, the vertical outlet channel and the horizontal channel.

In another aspect of the present application, a method for forming a semiconductor structure that is capable of real-time spatial sensing of nanoparticles within a nanofluid is provided. In one embodiment of the present application, the method of the present application includes forming an array of gate structures on a portion of a topmost semiconductor layer of a semiconductor-on-insulator substrate. Portions of a handle substrate of the semiconductor-on-insulator substrate that are located at both ends of the array of gate structures are then exposed. Next, an interlevel dielectric material is formed on the exposed portions of the handle substrate and surrounding the array of gate structures. Vertical channels are formed within the interlevel dielectric material and they expose sidewall surfaces of an insulator layer of the semiconductor-on-insulator substrate that is positioned directly beneath the array of gate structures. The insulator layer that is positioned directly beneath the array of gate structures is then removed to provide a horizontal channel connected to the vertical channels. A back gate dielectric material portion is then formed that lines exposed surfaces within the verticals channel, and the horizontal channel.

In yet another aspect of the present application, a method of sensing nanoparticles within a nanofluid is provided. In one embodiment of the present application, the method includes providing a nanofluid sensor as described above. Next, a nanofluid containing nanoparticles is added into the vertical inlet channel. The added nanofluid is then flown through the vertical inlet channel and into the horizontal channel. As the nanofluid passes through the horizontal channel, the characteristics of each gate structure of the array of gate structures is measured and recorded.

DESCRIPTION

Figure 1:
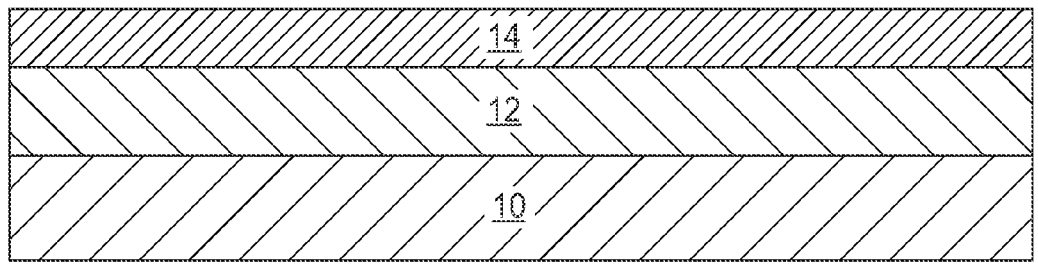
FIG. 1 is a cross sectional view of an exemplary semiconductor structure including a semiconductor-on-insulator substrate that can be employed in accordance with an embodiment of the present application.

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements in the various embodiments of the present application are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application. For purposes of the description hereinafter, the terms "upper", "lower", "right", "left", "vertical", "horizontal", "top", "bottom", and derivatives thereof shall relate to the disclosed structures and methods, as oriented in the drawing figures.

Referring first to FIG. 1, there is illustrated an exemplary semiconductor structure that can be employed in accordance with an embodiment of the present application. The exemplary semiconductor structure that is shown in FIG. 1 is a semiconductor-on-insulator (SOI) substrate that includes, from bottom to top, a handle substrate 10, an insulator layer 12 located directly upon a surface of the handle substrate 10, and a topmost semiconductor layer 14 located directly on a surface of the insulator layer 12. The handle substrate 10 of the SOI substrate shown in FIG. 1 provides mechanical support for the insulator layer 12 and the topmost semiconductor layer 14.

In one embodiment of the present application, the handle substrate 10 and the topmost semiconductor layer 14 of the SOI substrate may comprise a same semiconductor material. In another embodiment of the present application, the handle substrate 10 and the topmost semiconductor layer 14 of the SOI substrate may comprise a different semiconductor material. The term "semiconductor" as used herein in connection with the semiconductor material of the handle substrate 10 and the topmost semiconductor layer 14 denotes any semiconductor material including, for example, Si, Ge, SiGe, SiC, SiGeC, and III/V compound semiconductors such as, for example, InAs, GaAs, or InP. Multilayers of these semiconductor materials can also be used as the semiconductor material of the handle substrate 10 and the topmost semiconductor layer 14. The semiconductor material that can be used in providing the handle substrate 10 and/or the topmost semiconductor layer 14 may be single crystalline, polycrystalline or amorphous. Typically, the semiconductor material that provides the handle substrate 10 and the topmost semiconductor layer 14 comprises a single crystalline semiconductor material such as, for example, single crystalline silicon.

In some embodiments, the handle substrate 10 and the topmost semiconductor layer 14 may have a same crystal orientation. In other embodiments, the handle substrate 10 and the topmost semiconductor layer 14 may have a different crystal orientation. The crystal orientation of the handle substrate 10 and/or the topmost semiconductor layer 14 may be {100}, {110}, or {111}. Other crystallographic orientations besides those specifically mentioned can also be used in the present application. In some embodiments (not shown), the topmost semiconductor layer 14 can be processed to include semiconductor regions having different crystal orientations.

The insulator layer 12 of the SOI substrate may be a crystalline or non-crystalline oxide or nitride. In one embodiment, the insulator layer 12 is an oxide such as, for example, silicon dioxide.

The SOI substrate may be formed utilizing standard processes including for example, SIMOX (separation by ion implantation of oxygen) or layer transfer. The thickness of the topmost semiconductor layer 14 of the SOI substrate can be from 1 nm to 10 nm. If the thickness of the topmost semiconductor layer 14 is not within the above mentioned range, a thinning step such as, for example, planarization or etching can be used to reduce the thickness of the topmost semiconductor layer 14 to a value within the range mentioned above. The insulator layer 12 of the SOI substrate typically has a thickness from 1 nm to 200 nm, with a thickness from 100 nm to 150 nm being more typical. The thickness of the handle substrate 10 of the SOI substrate is inconsequential to the present application.

Figure 2:
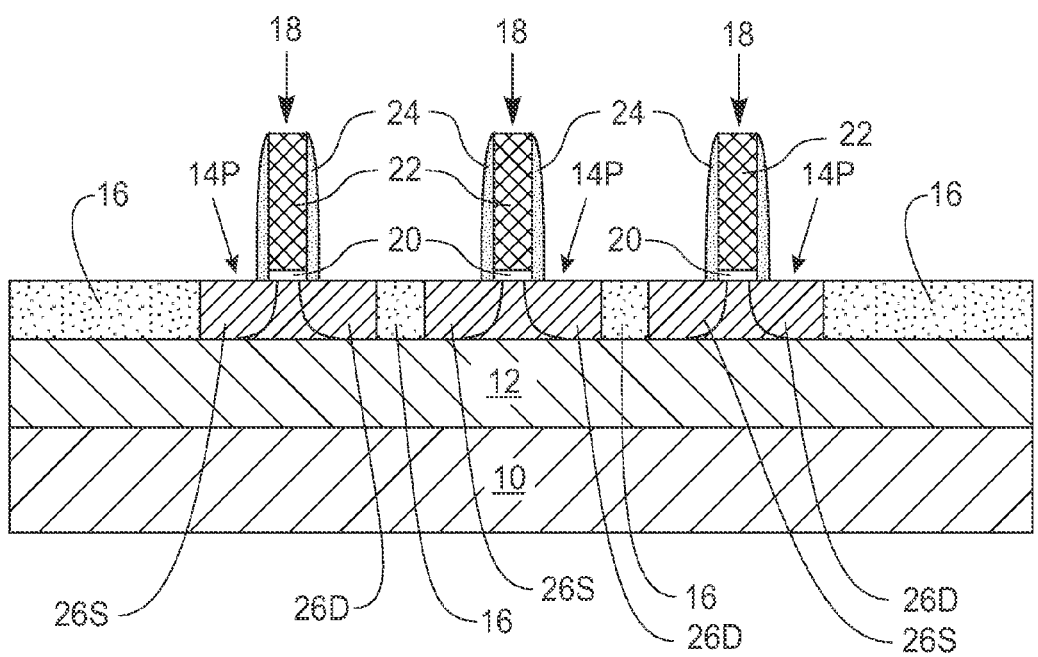
FIG. 2 is a cross sectional view of the exemplary semiconductor structure of FIG. 1 after forming an array of gate structures, wherein each gate structure of the array of gate structures is located on a remaining portion of the topmost semiconductor layer of the semiconductor-on-insulator substrate.

Referring now to FIG. 2, there is illustrated the exemplary semiconductor structure of FIG. 1 after forming an array of gate structures 18. Each gate structure 18 of the array of gate structures is located on a remaining portion of the topmost semiconductor layer 14 of the semiconductor-on-insulator substrate. Each remaining portion of the topmost semiconductor layer 14 that includes a gate structure 18 may be referred to herein as a semiconductor material portion 14P.

As is shown in FIG. 2, each semiconductor material portion 14P, and hence each gate structure 18, is separated from each other by a trench isolation structure 16. Each trench isolation structure 16 that is formed has a topmost surface that is coplanar with a topmost surface of each semiconductor material portion 14P, and a bottommost surface that is in direct physical contact with a topmost surface of insulator layer 12. The trench isolation structure 16 can be formed utilizing a conventional trench isolation process well known to those skilled in the art. For example, lithography, etching and filling of the trench with a trench dielectric such as an oxide may be used in forming each trench isolation structure 16. Optionally, a liner may be formed in the trench prior to trench fill, a densification step may be performed after the trench fill and a planarization process may follow the trench fill as well.

In one embodiment of the present application, each gate structure 18 of the array of gate structures that is provided is a sacrificial gate structure. By "sacrificial gate structure" it is meant a gate structure that does not operate as a functional gate structure (to be subsequently defined). In another embodiment of the present application, each gate structure 18 of the array of gate structure is a functional gate structure. By "functional gate structure" it is meant a gate structure that is used to control output current (i.e., flow of carriers in a channel region) of a semiconductor device through electrical or magnetic currents. The functional gate structures that can be used as the gate structures 18 of the array of gate structures can be formed by a gate-first process or a gate-last process. In a gate-first process, the functional gate structures are formed first, followed by the source region and drain region. In a gate-last process, the functional gate structures are formed after the source region and drain region are formed. In a gate-last process, sacrificial gate structures can be formed first, followed by formation of the source region and the drain region and thereafter each sacrificial gate structure is replaced by a functional gate structure.

Notwithstanding the type of gate structure (i.e., sacrificial or functional), each gate structures 18 includes a front gate dielectric material portion 20 and a front gate material portion 22. In some embodiments (and as shown), the front gate dielectric material portion 20 and the front gate material portion 22 of the sacrificial gates or functional gates are vertically stacked one atop the other. In other embodiments (not shown), and only when a functional gate structure is formed utilizing a gate-last process, the front gate dielectric material portion 20 can be U-shaped and the front gate material portion 22 can be contained within the U-shaped gate dielectric material portion. In such an embodiment, the topmost surface of each vertical portion of the U-shaped gate dielectric material portion is coplanar with a topmost surface of the front gate material portion 22. For reference, the gate structure 50 shown in FIG. 11 denotes a gate structure that contains a U-shaped gate dielectric material portion (i.e., element 52) that surrounds the gate material portion (i.e., 54).

The front gate dielectric material that provides each front gate dielectric material portion 20 can be an oxide, nitride, and/or oxynitride. In one example, the front gate dielectric material that provides each front gate dielectric material portion 20 can be a high-k material having a dielectric constant greater than silicon dioxide. Exemplary high-k dielectrics include, but are not limited to, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, SiON, $SiN_x$, a silicate thereof, and an alloy thereof. Each value of x is independently from 0.5 to 3 and each value of y is independently from 0 to 2. In some embodiments, a multilayered gate dielectric structure comprising different gate dielectric materials, e.g., silicon dioxide, and a high-k gate dielectric can be used in providing each front gate dielectric material portion 20.

The front gate dielectric material used in providing each front gate dielectric material portion 20 can be formed by any deposition technique including, for example, chemical vapor deposition (CVD), plasma enhanced chemical vapor deposition (PECVD), physical vapor deposition (PVD), sputtering, or atomic layer deposition. In some embodiments, a thermal process including, for example, thermal oxidation and/or thermal nitridation may be used in forming each front gate dielectric material portion 20. In one embodiment of the present application, the front gate dielectric material used in providing each front gate dielectric material portion 20 can have a thickness in a range from 1 nm to 10 nm. Other thicknesses that are lesser than or greater than the aforementioned thickness range can also be employed for the gate dielectric material.

In embodiments when each gate structure 18 is a functional gate structure, each front gate material portion 22 comprises a gate conductor material. The gate conductor material used in providing each front gate material portion 22 of each functional gate structure can include any conductive material including, for example, doped polysilicon, an elemental metal (e.g., tungsten, titanium, tantalum, aluminum, nickel, ruthenium, palladium and platinum), an alloy of at least two elemental metals, an elemental metal nitride (e.g., tungsten nitride, aluminum nitride, and titanium nitride), an elemental metal silicide (e.g., tungsten silicide, nickel silicide, and titanium silicide) or multilayered combinations thereof. In some embodiments, each front gate material portion 22 may comprise an nFET gate metal. In other embodiments, each front gate material portion 22 may comprise a pFET gate metal.

The gate conductor material used in providing each front gate material portion 22 of each functional gate structure can be formed utilizing a deposition process including, for example, chemical vapor deposition (CVD), plasma enhanced chemical vapor deposition (PECVD), physical vapor deposition (PVD), sputtering, atomic layer deposition (ALD) or other like deposition processes. When a metal silicide is formed, a conventional silicidation process is employed. In one embodiment of the present application, the front gate material used in providing each front gate material portion 22 of each functional gate structure can have a thickness in a range from 50 nm to 100 nm. Other thicknesses that are lesser than or greater than the aforementioned thickness range can also be employed for the gate material portion.

In embodiments when each gate structure 18 is a sacrificial gate structure, each front gate material portion 22 is comprised of sacrificial gate material portion selected from polysilicon, and a metal such as, for example, tungsten, aluminum or copper. These materials can be formed by a deposition process such as, for example, chemical vapor deposition and plasma enhanced chemical vapor deposition. In one embodiment of the present application, the sacrificial gate material used in providing each front gate material portion 22 of each sacrificial gate structure can have a thickness in a range from 50 nm to 100 nm. Other thicknesses that are lesser than or greater than the aforementioned thickness range can also be employed for the sacrificial gate material portion.

After providing each gate structure 18, a dielectric spacer material such as, for example, silicon dioxide, silicon nitride, and/or silicon oxynitride, can be formed on exposed sidewall surfaces of each gate structure 18 and thereafter the dielectric spacer material can be etched to form dielectric spacers 24 on the exposed sidewall surfaces of each gate structure 18.

The exemplary structure shown in FIG. 2 also includes a source region 26S located within each semiconductor material portion 14P and on one side of each gate structure 18, and a drain region 26D located within each semiconductor material portion 14P and on another side of each gate structure 18. The source/drain regions can be formed by introducing a dopant into the exposed portions of each semiconductor material portion 14P. The dopant can be n-type or p-type. The term "p-type" refers to the addition of impurities to an intrinsic semiconductor that creates deficiencies of valence electrons. Examples of p-type dopants, i.e., impurities, include, but are not limited to, boron, aluminum, gallium and indium. "N-type" refers to the addition of impurities that contributes free electrons to an intrinsic semiconductor. Examples of n-type dopants, i.e., impurities, include, but are not limited to, antimony, arsenic and phosphorous. In some embodiments, the dopant may be introduced into the exposed portions of each semiconductor material portion 14P, by ion implantation, plasma doping or gas phase doping. The concentration of dopants used in providing the source/drain regions can range from 5e18 atoms/cm$^3$ to 1.5e21 atoms/cm$^3$. Although not shown, in some embodiments the source/drain regions may include epitaxial semiconductor materials grown either on top of the topmost semiconductor layer 14 or embedded in the topmost semiconductor layer 14. The epitaxy semiconductor materials, if present, improve the device performance by reducing the external resistance. The epitaxial semiconductor materials may be in-situ or ex-situ doped. Although not specifically labeled, the portion of each semiconductor material portion 14P that is located directly beneath each gate structure 18 and that is located between the source region 26S and the drain region 26D can be referred to a semiconductor channel (or body) region.

Figure 3:
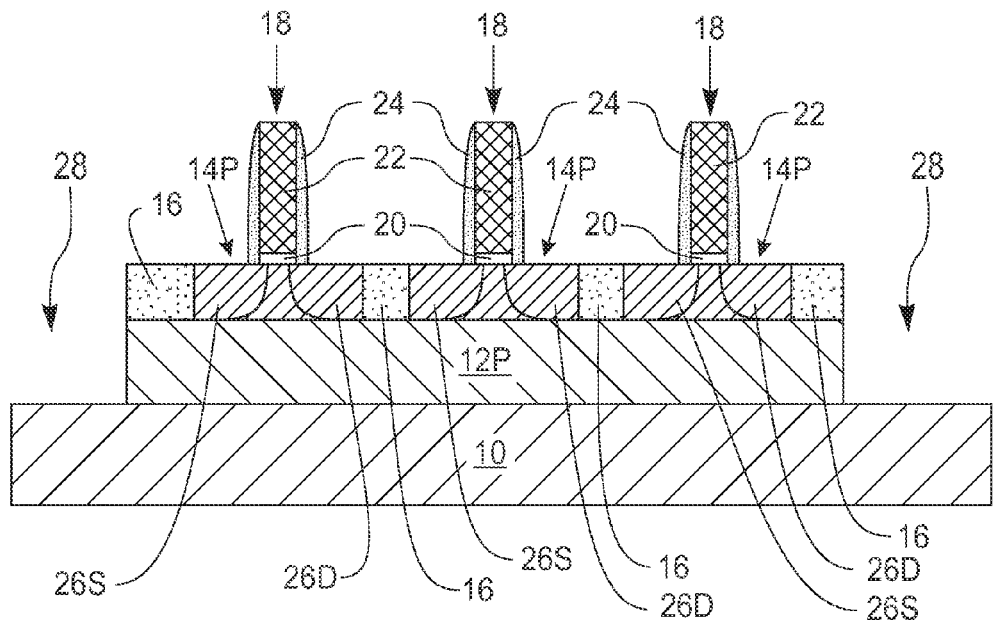
FIG. 3 is a cross sectional view of the exemplary semiconductor structure of FIG. 2 after exposing portions of the handle substrate of the semiconductor-on-insulator substrate.

Referring now to FIG. 3, there is illustrated the exemplary semiconductor structure of FIG. 2 after exposing portions of the handle substrate 10 of the semiconductor-on-insulator substrate. In FIG. 3, reference numeral 28 shows the location of the structure in which the handle substrate 10 is now exposed by removing portions of the trench isolation structure 16 and removing underlying portions of the insulator layer 12. The remaining portion of the insulator layer that is located directly beneath each gate structure 18 may be referred to herein as an insulator layer portion 12P. As shown, sidewall surfaces of the isolation layer portion 12P are now exposed.

In the present application, lithography and etching can be used in exposing portions of the handle substrate 10. In one embodiment, the etching step that is used to provide the structure shown in FIG. 3 can include an anisotropic dry etching process such as, for example, reactive ion etching. In another embodiment, the etching step that is used to provide the structure shown in FIG. 3 can include an anisotropic wet etching process. In some embodiments, a single etch can be used. In other embodiments, a combination of etching processes can be used. After etching, the photoresist mask that is provided by the lithographic step can be removed by utilizing a conventional resist stripping process such as, for example, ashing.

Figure 4:
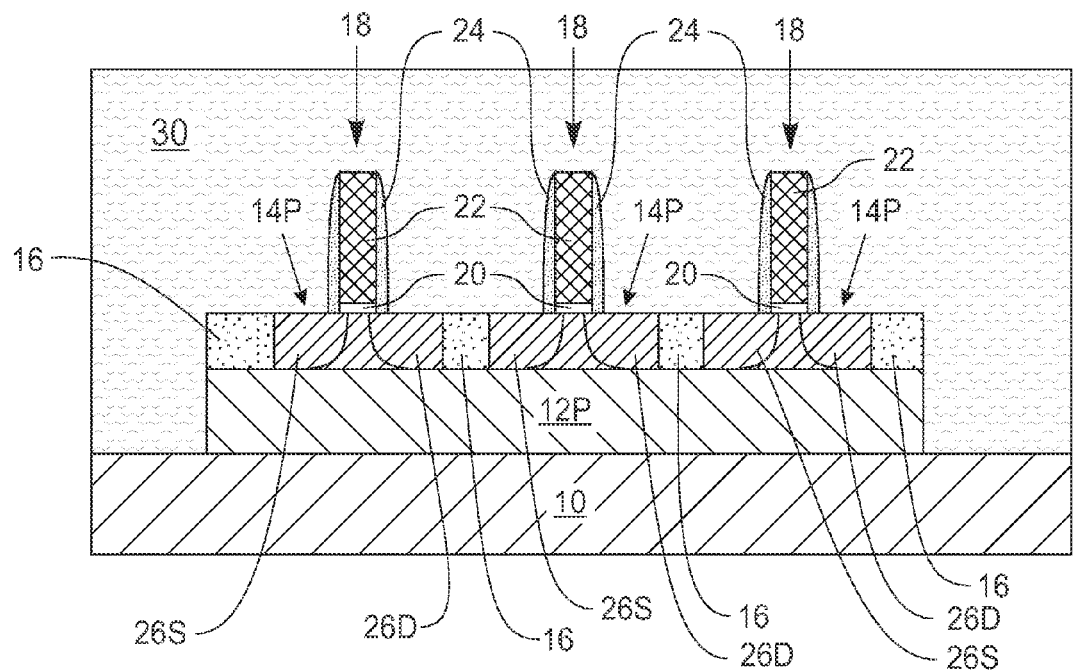
FIG. 4 is a cross sectional view of the exemplary semiconductor structure of FIG. 3 after forming an interlevel dielectric material.

Referring now to FIG. 4, there is illustrated the exemplary semiconductor structure of FIG. 3 after forming an interlevel dielectric material 30. As is shown, the interlevel dielectric material 30 covers the exposed portions of the handle substrate 10 and is formed surrounding each gate structure 18. As is also shown, the interlevel dielectric material 30 is formed on exposed sidewall surfaces of the insulator layer portion 12P.

In some embodiments, the interlevel dielectric material 30 may be composed of, for example, silicon dioxide, silicon nitride, undoped silicate glass (USG), fluorosilicate glass (FSG), borophosphosilicate glass (BPSG), a spin-on low-k dielectric layer, a chemical vapor deposition (CVD) low-k dielectric layer or any combination thereof. The term "low-k" as used throughout the present application denotes a dielectric material that has a dielectric constant of less than silicon dioxide. In one embodiment, the interlevel dielectric material 30 can be formed utilizing a deposition process including, for example, chemical vapor deposition (CVD), plasma enhanced chemical vapor deposition (PECVD), evaporation or spin-on coating.

Figure 5:
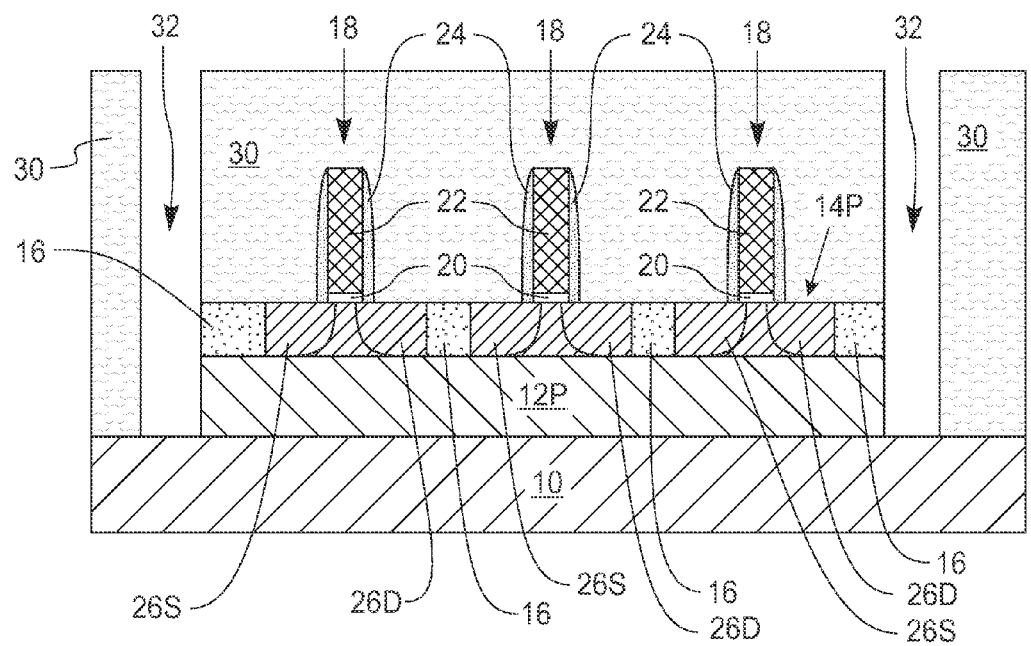
FIG. 5 is a cross sectional view of the exemplary semiconductor structure of FIG. 4 after forming vertical channels within the interlevel dielectric material that expose a sidewall surface of the insulator layer of the semiconductor-on-insulator substrate.

Referring now to FIG. 5, there is illustrated the exemplary semiconductor structure of FIG. 4 after forming vertical channels 32 within the interlevel dielectric material 30 that expose the sidewall surface of the insulator layer portion 12P of the semiconductor-on-insulator substrate. The vertical channels 32 can be formed by lithography and an anisotropic etching process which is selective in removing exposed portions of the interlevel dielectric material 30. As is shown, the vertical channels 32 also re-expose a portion of the handle substrate 10.

Figure 6:
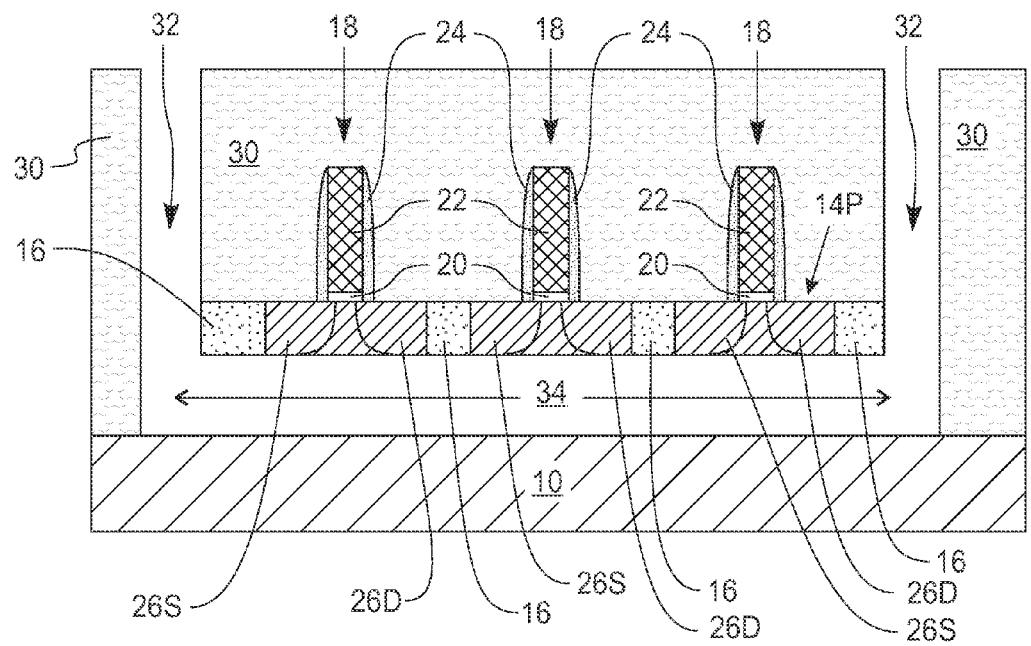
FIG. 6 is a cross sectional view of the exemplary semiconductor structure of FIG. 5 after completely removing the insulator layer from beneath the array of gate structures to provide a horizontal channel.

Referring now to FIG. 6, there is illustrated the exemplary semiconductor structure of FIG. 5 after completely removing the insulator layer portion 12P from beneath the array of gate structures 18 to provide a horizontal channel 34. The horizontal channel 34 is connected to each vertical channel 32. Also, the horizontal channel 34 exposes a bottommost surface of each trench isolation structure 16, a bottommost surface of each source region 26S, a bottommost surface of each drain region 26D and a bottommost surface of each semiconductor material portion 14P. The horizontal channel 34 further exposes a portion of a topmost surface of the handle substrate 10. The horizontal channel 34 can be formed utilizing a wet isotropic etch process such as, for example, a hydrofluoric acid wet etch process. It is noted that the upper portion of the structure shown in FIG. 6 is not floating. Instead, end portions that run into an out of the plane of the paper are anchored to portions of the original SOI substrate.

Figure 7:
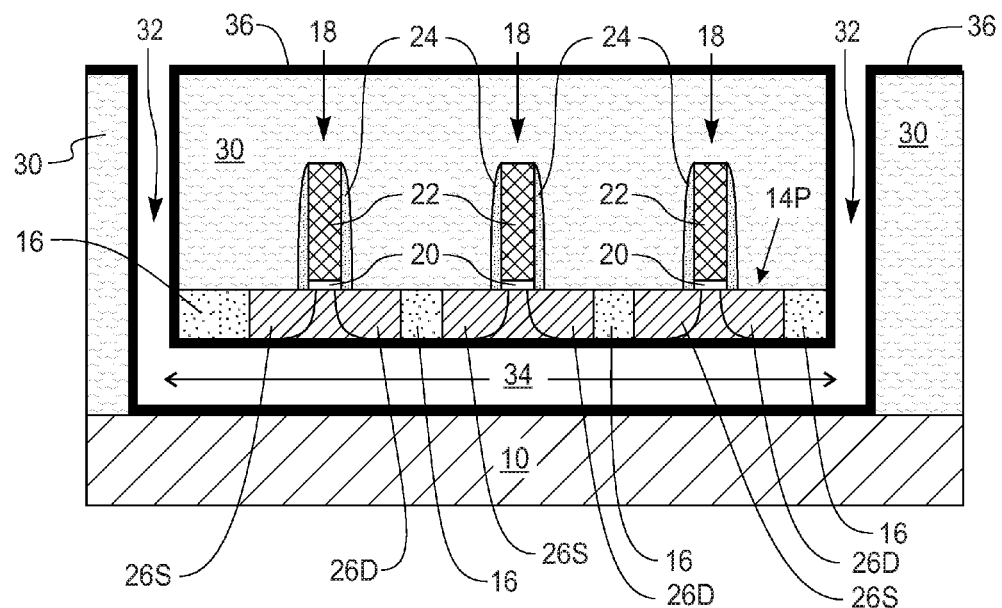
FIG. 7 is a cross sectional view of the exemplary semiconductor structure of FIG. 6 after forming a back gate dielectric material.

Referring now to FIG. 7, there is illustrated the exemplary semiconductor structure of FIG. 6 after forming a back gate dielectric material 36. The back gate dielectric material 36 is formed on exposed surfaces of the interlevel dielectric material 30 that are within and outside the vertical channels 32, on the exposed bottommost surfaces of each of the trench isolation structures 16, source regions 26S, drain regions 26D and semiconductor material portions 14P that are located within the horizontal channel 34, and on the exposed topmost surface of the handle substrate 10 within the vertical channels 32 and the horizontal channel 34.

The back gate dielectric material 36 may include one of gate dielectric materials used in providing the front gate dielectric material portion 20. In one embodiment, the back gate dielectric material 36 comprises a same gate dielectric material as the front gate dielectric material portion 20. In another embodiment, the back gate dielectric material 36 comprises a different gate dielectric material as the front gate dielectric material portion 20. The back gate dielectric material 36 typically is comprised of a high-k dielectric such as, for example, $HfO_2$, $ZrO_2$, $La_2O_3$, $Al_2O_3$, $TiO_2$, $SrTiO_3$, $LaAlO_3$, $Y_2O_3$, $HfO_xN_y$, $ZrO_xN_y$, $La_2O_xN_y$, $Al_2O_xN_y$, $TiO_xN_y$, $SrTiO_xN_y$, $LaAlO_xN_y$, $Y_2O_xN_y$, SiON, $SiN_x$, a silicate thereof, and an alloy thereof. Each value of x is independently from 0.5 to 3 and each value of y is independently from 0 to 2.

The back gate dielectric material 36 can be formed by any conformal deposition technique including, for example, chemical vapor deposition (CVD), plasma enhanced chemical vapor deposition (PECVD), or atomic layer deposition. In one embodiment of the present application, the back gate dielectric material 36 can have a thickness in a range from 1 nm to 10 nm. Other thicknesses that are lesser than or greater than the aforementioned thickness range can also be employed for the back gate dielectric material 36.

Figure 8:
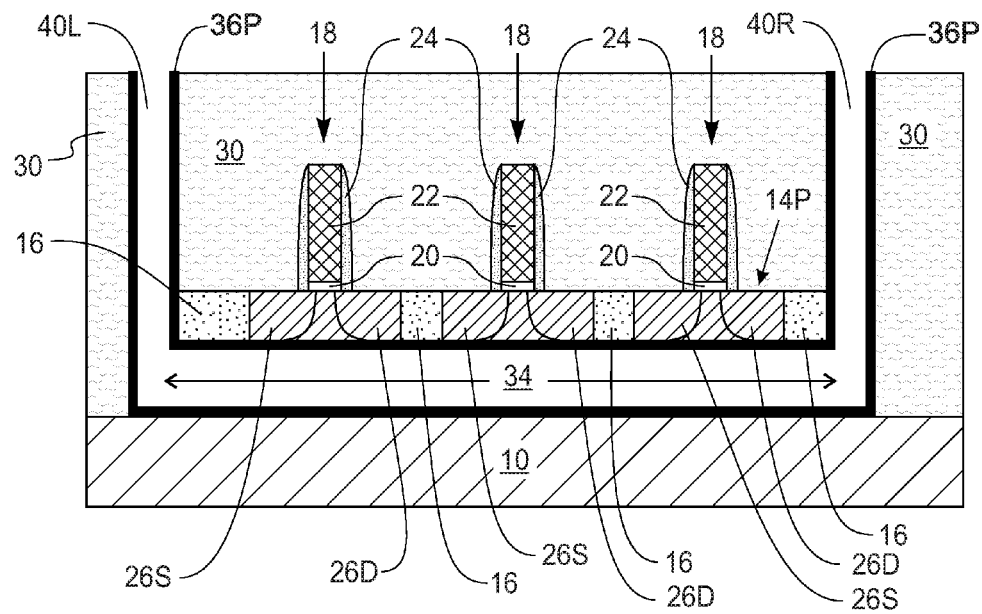
FIG. 8 is a cross sectional view of the exemplary semiconductor structure of FIG. 7 after removing the back gate dielectric material from an uppermost surface of the interlevel dielectric material.

Referring now to FIG. 8, there is illustrated the exemplary semiconductor structure of FIG. 7 after removing the back gate dielectric material 36 from an uppermost surface of the interlevel dielectric material 30 to provide a back gate dielectric material portion 36P. In some embodiments of the present application, this step of removing the back gate dielectric material 36 from an uppermost surface of the interlevel dielectric material 30 can be omitted.

The back gate dielectric material portion 36P is present on exposed surfaces of the dielectric material 30 that are within the vertical channels 32, on the exposed bottommost surfaces of each of the trench isolation structures 16, source regions 26S, drain regions 26D and semiconductor material portions 14P that are located within the horizontal channel 34, and on the exposed topmost surface of the handle substrate 10 within the vertical channels 32 and the horizontal channel 34. The removal of the back gate dielectric material 36 from an uppermost surface of the interlevel dielectric material 30 may comprise a planarization process such as, for example, chemical mechanical planarization and/or grinding.

FIGS. 7-8 show the semiconductor structure of the present application. Notably, FIGS. 7-8 shown a structure that includes an array of gate structures 18, each gate structure 18 of the array of gate structures is located on a semiconductor material portion 14P. An interlevel dielectric material 30 surrounds the array of gate structures. The structure includes a vertical inlet channel 40L (previous left hand vertical channel 32) located within a portion of the interlevel dielectric material 30 and located on one side of the array of gate structures 18. A vertical outlet channel 40R (previous right hand vertical channel 32) located within another portion of the interlevel dielectric material 30 and located on another side of the array of gate structures 18. Horizontal channel 34 is connected to the vertical inlet channel 40L and vertical outlet channel 40R. The horizontal channel 34 is also located beneath the array of gate structures 18, and it vertically separates the array of gate structures 18 from an underlying handle substrate 10. Horizontal channel 34 is also in fluid communication with the vertical inlet channel 40L and the vertical outlet channel 40R. During operation, the horizontal channel 34 serves as a back gate of the structure. A back gate dielectric material portion 36P contiguously lines exposed surfaces within the vertical inlet channel 40L, the vertical outlet channel 40R and the horizontal channel 34.

The semiconductor structure shown in FIGS. 7-8 is capable of real-time spatial sensing of nanosized particles (i.e., nanoparticles) within a nanofluid which contains the nanoparticles. In some embodiments, a single set of nanoparticles can be sensed utilizing the semiconductor structure shown in FIGS. 7-8. In another embodiment, at least a first set of nanoparticles and a second set of nanoparticles which differs from the first set of nanoparticles can be sensed utilizing the semiconductor structure of the present application. In other embodiments, any number of sets of nanoparticles that differ from each other can be sensed utilizing the semiconductor structure of the present application.

The term "nanoparticles" denotes particles that have a size from 1500 nm or less. Typically, the nanoparticles have a particle size from 10 nm to 100 nm. The type of nanoparticles that can be sensed utilizing the semiconductor structure of the present application is not limited to any specific types. Thus, the nanoparticles that can be sensed by the semiconductor structure of the present application can be metallic, semi-metallic, magnetic, non-magnetic, organometallic, organic, and any combination thereof. In some embodiments, the nanoparticles that are sensed are biomolecules such as, for example, proteins, polysaccharides, lipids, and nucleic acids, as well as small molecules such as primary metabolites, secondary metabolites, and natural products. In one embodiment, the nanoparticles are DNA nanoparticles.

In some embodiments of the present application, the nanoparticles that can be sensed by the semiconductor structure of the present application are negatively charge. In other embodiments of the present application, the nanoparticles that can be sensed by the semiconductor structure of the present application are positively charged. In yet other embodiments of the present application, some of the nanoparticles that can be sensed by the semiconductor structure of the present application are positively charged, while other nanoparticles that can be sensed are negatively charged.

The nanoparticles can be present in a cosmetic formulation or composition, a pharmaceutical formulation or composition, a hair care formulation or composition, a household care or industrial care formulation or composition, or other formulations or compositions in which nanoparticles are present.

The nanoparticles are typically present in the nanofluid (i.e., base fluid) as a colloidal suspension. The nanofluid that contains the nanoparticles may include a base fluid such as, for example, water, alcohols, esters, hydrocarbons, ethers, and oils.

Figure 9A:
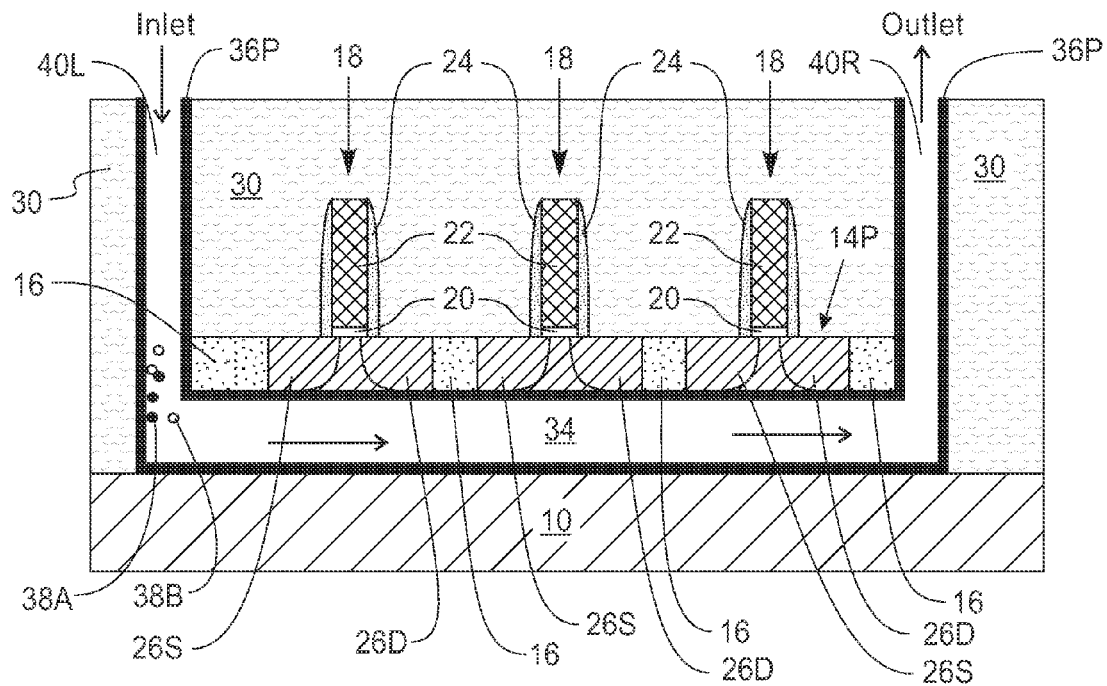
FIGS. 9A, 9B and 9C are cross sectional views of the exemplary semiconductor structure of FIG. 8 after adding a nanofluid containing a first and second set of nanoparticles into the vertical channels and horizontal channels and after various time intervals.
Figure 9B:
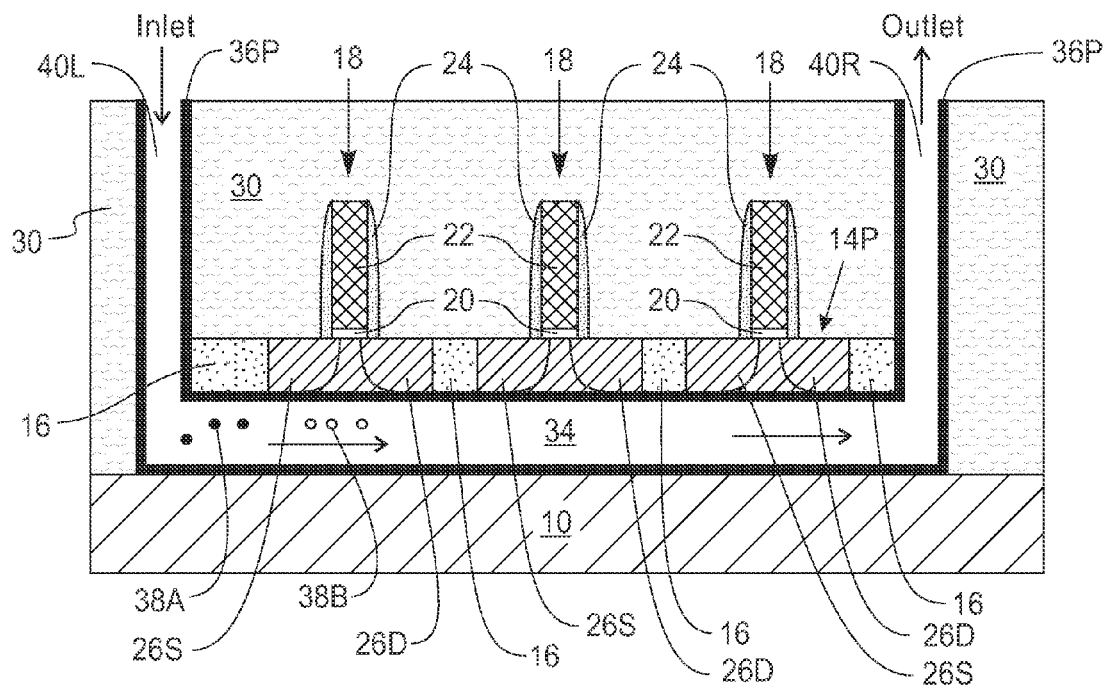
Figure 9C:
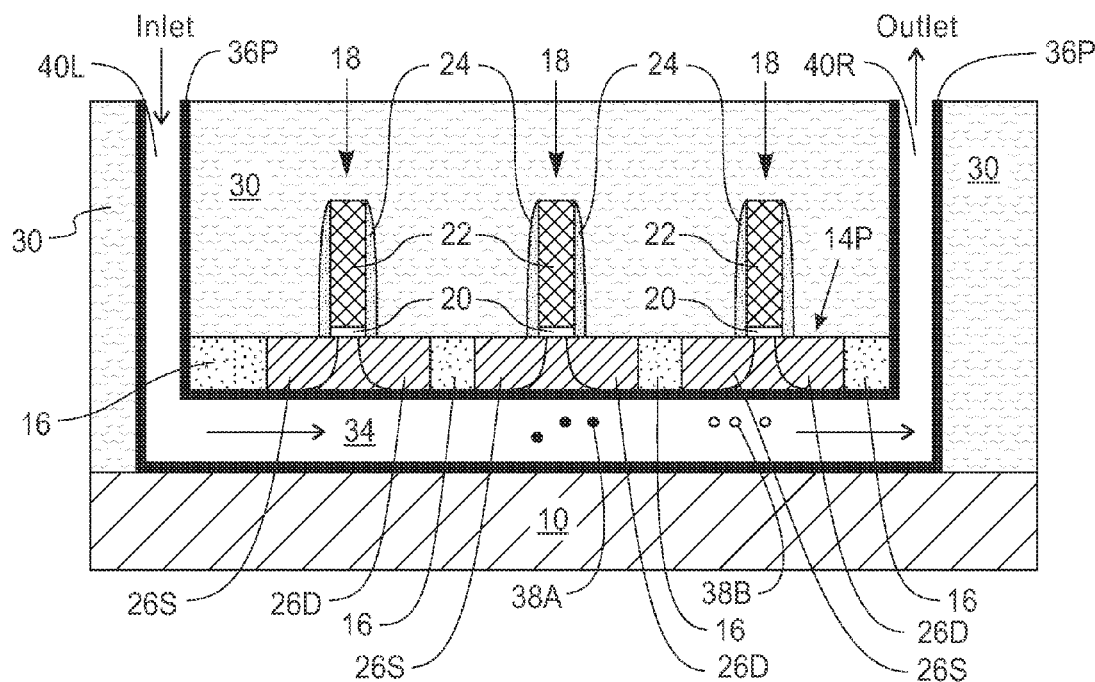

Referring now to FIGS. 9A, 9B and 9C, there are illustrated the exemplary semiconductor structure of FIG. 8 after adding a nanofluid containing a first set of nanoparticles 38A and a second set of nanoparticles 38B into the input vertical channel 40L and allowing the same to flow into the horizontal channel 34 for sensing. For clarity, the drawings of the present application do not shown the presence of pumps, reservoirs, piping, tubing, flow controls, bubblers, injection valves, gas sources, and other like components that would be necessary to introduce and flow a nanofluid through the semiconductor structure of the present application.

In this exemplary embodiment, the first set of nanoparticles 38A has a different flow rate in the nanofluid than the second set of nanoparticles 38B. As the nanofluid flows through the horizontal channel 34, i.e., the back gate, nanoparticles with different flow rates get to the different back gate regions of different gate structures at different time intervals, resulting in the change of the gate structures characteristics. By recording each gate structure's characteristics as a function of time, one can extrapolate the information of the nanoparticles in the nanofluid.

Notably, FIG. 9A shows the semiconductor structure at time, t, equal to zero. As this point of the sensing process all the gate structures 18 are turned off. Also, and during this period of time there is sufficient time and space within the input vertical channel 40L and horizontal channel 34 to allow for separation of the various nanoparticles. FIG. 9B shows the semiconductor structure at time, t, equal to t1. As shown, the first set of nanoparticles 38A separates from the second set of nanoparticles 38B given the different flow rates of the different nanoparticles. At t1, and by way of an example, the set second of nanoparticles 38B are located directly beneath the first gate structure 18 (far left hand gate structure), and the first gate structure is turned on, while the others remain off. FIG. 9C shows the semiconductor structure at another time, tn, during the flow of the nanoparticles 28A and 28B within the horizontal channel 34. At tn, the first gate structure (i.e., the far left hand gate structure) is turned off, while the middle gate structure is on with a current $I_{(n-1)}$ and the last gate structure (i.e., far right gate structure) is also turned on with current $I_n$. At tn, the middle gate structure senses the first set of nanoparticles 38A, while the last gate structure (i.e., the far right gate structure) senses the second set of nanoparticles 38B.

Figure 10:
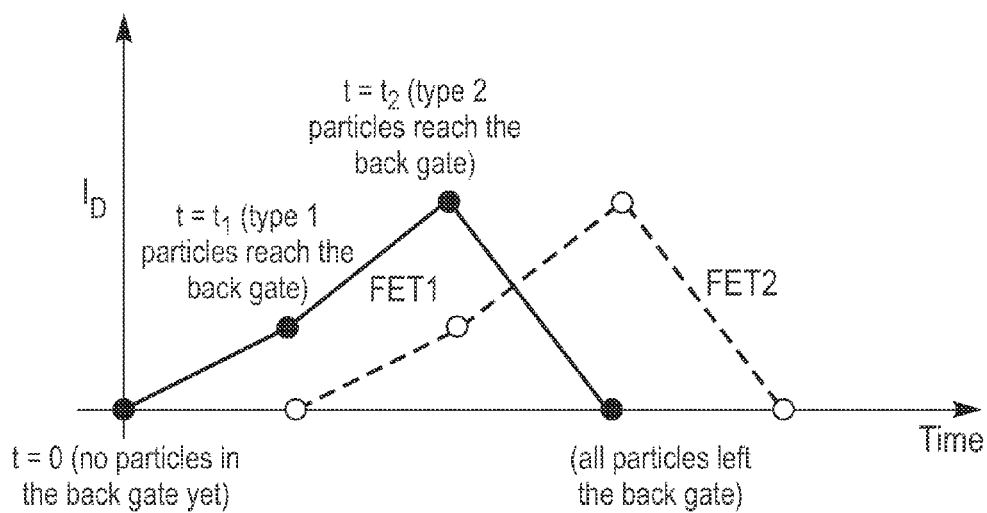
FIG. 10 is a graph of drain current, Id, versus time, t as determined by two of the gate structures of the exemplary semiconductor structures shown in FIGS. 9A, 9B and 9C.

Referring now to FIG. 10, there is illustrated a graph of drain current, Id, versus time, t as determined by two of the gate structures of the exemplary semiconductor structures shown in FIGS. 9A, 9B and 9C. In this drawing FET 1 refers to the far left hand gate structure in FIGS. 9A, 9B and 9C, while FET 2 denotes the middle gate structure shown in FIGS. 9A, 9B and 9C.

Figure 11:
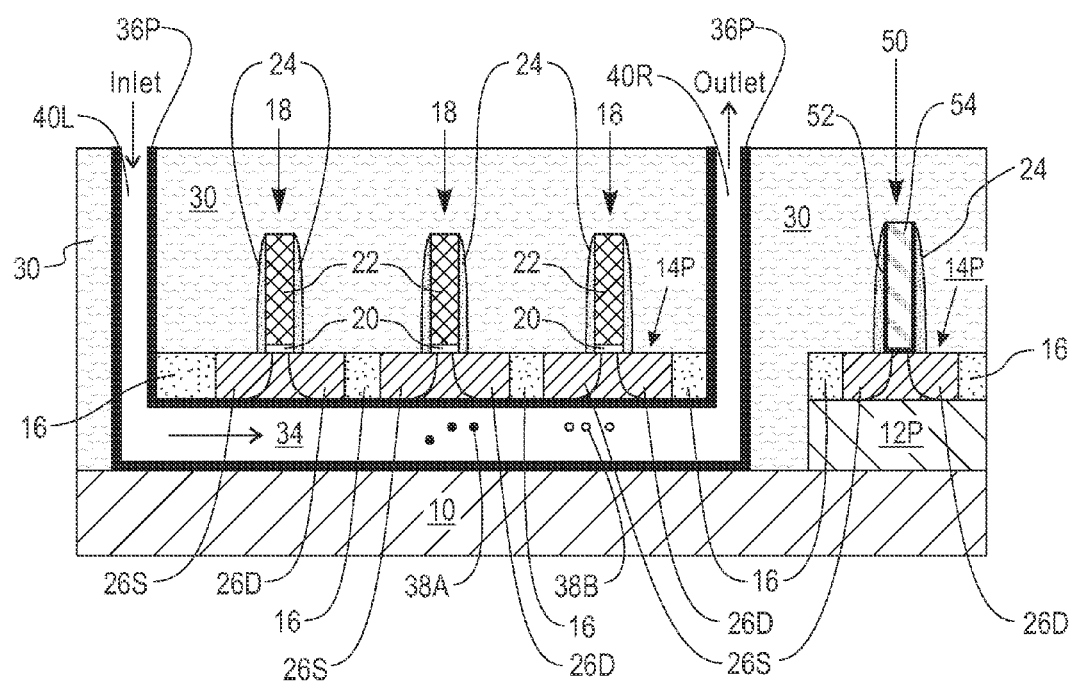
FIG. 11 is a cross sectional view of the exemplary semiconductor structure of FIG. 8 integrated with a logic gate structure in accordance with another embodiment of the present application.

Referring to FIG. 11, there is illustrated the exemplary semiconductor structure of FIG. 8 integrated with a logic gate structure 50 in accordance with another embodiment of the present application. The logic gate structure 50 includes a U-shaped gate dielectric material portion 52 surrounding a gate material portion 54. In some embodiments, a non U-shaped gate dielectric material portion may be used instead of the U-shaped gate dielectric material portion 52 shown in FIG. 11. The U-shaped gate dielectric material portion 52 (or the non U-shaped gate dielectric material portion) may include one of the dielectric materials mentioned above in providing the front gate dielectric material portion 20. The gate material portion 54 may comprise one of the gate conductor materials mentioned above in providing the front gate material portion 22. In this embodiment, the logic gate structure 50 is located on remaining portion of the insulator layer 12 (i.e., insulator layer portion 12P). The logic gate structure 50 can be formed prior to or after forming the array of gate structures 18 utilizing a replacement gate process, i.e., gate last process, known to those skilled in the semiconductor industry.

While the present application has been particularly shown and described with respect to various embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed as new is:

1. A semiconductor structure comprising:
   a nanofluid sensor for sensing nanoparticles in a nanofluid, said nanofluid sensor comprising:
   an array of gate structures, each gate structure of the array of gate structures is located on a semiconductor material portion;
   an interlevel dielectric material surrounding said array of gate structures;
   a vertical inlet channel located within a portion of said interlevel dielectric material and located on one side of said array of gate structures;
   a vertical outlet channel located within another portion of said interlevel dielectric material and located on another side of said array of gate structures;
   a horizontal channel connected to said vertical inlet and outlet channels, located beneath said array of gate structures, and vertically separating said array of gate structures from an underlying handle substrate; and
   a back gate dielectric material portion lining the entirety of exposed surfaces within each of said vertical inlet channel, said vertical outlet channel and said horizontal channel, and said back gate dielectric material portion extends to at least a topmost surface of said interlevel dielectric material.

2. The semiconductor structure of claim 1, wherein said array of gate structures are sacrificial gate structures.

3. The semiconductor structure of claim 2, wherein each sacrificial gate structure comprises, from bottom to top, a front gate dielectric material portion and a front sacrificial gate material portion.

4. The semiconductor structure of claim 2, further comprising a dielectric spacer located on sidewall surfaces of each sacrificial gate structure.

5. The semiconductor structure of claim 2, further comprising a trench isolation structure separating each sacrificial gate structure of said array of gate structures.

6. The semiconductor structure of claim 2, further comprising a source region located within each semiconductor material portion and on one side of each sacrificial gate structure, and a drain region located within each semiconductor material portion and on another side of each sacrificial gate structure.

7. The semiconductor structure of claim 2, further comprising a logic gate structure located laterally adjacent said array of gate structures, said logic gate structure is present on another semiconductor material portion, and wherein an insulator layer portion is located directly beneath said another semiconductor material portion.

8. The semiconductor structure of claim 1, wherein said array of gate structures are functional gate structures comprising a front gate dielectric material portion and a front gate material portion.

9. The semiconductor structure of claim 8, further comprising a dielectric spacer located on sidewall surfaces of each gate structure.

10. The semiconductor structure of claim 8, further comprising a trench isolation structure separating each functional structure of said array of gate structures.

11. The semiconductor structure of claim 8, further comprising a source region located within each semiconductor material portion and on one side of each functional gate structure, and a drain region located within each semiconductor material portion and on another side of each functional gate structure.

12. The semiconductor structure of claim 8, further comprising a logic gate structure located laterally adjacent said array of gate structures, said logic gate structure is present on another semiconductor material portion, and wherein an insulator layer portion is located directly beneath said another semiconductor material portion.

13. The semiconductor structure of claim 1, wherein said back gate dielectric material portion has a topmost surface that is coplanar with said topmost surface of said interlevel dielectric material.

14. The semiconductor structure of claim 1, wherein said back gate dielectric material portion is present on said topmost surface of said interlevel dielectric material.

* * * * *